United States Patent [19]
Alakhov et al.

[11] Patent Number: 5,478,730
[45] Date of Patent: Dec. 26, 1995

[54] METHOD OF PREPARING POLYPEPTIDES IN CELL-FREE TRANSLATION SYSTEM

[75] Inventors: July B. Alakhov; Vladimir I. Baranov; Sergei J. Ovodov; Ljubov A. Ryabova, all of Puschino; Alexandr S. Spirin, Moscow; Igor J. Morozov, Puschino, all of U.S.S.R.

[73] Assignee: Institute of Protein Research, Moscow Region, U.S.S.R.

[21] Appl. No.: 991,757

[22] Filed: Dec. 16, 1992

Related U.S. Application Data

[63] Continuation of Ser. No. 899,826, Jun. 16, 1992, abandoned, which is a continuation of Ser. No. 441,071, Nov. 22, 1989, abandoned, which is a continuation-in-part of Ser. No. 294,551, Dec. 21, 1988, abandoned.

[30] Foreign Application Priority Data

Dec. 22, 1988 [SU] U.S.S.R. ................................. 4618624
Jul. 31, 1989 [SU] U.S.S.R. ................................. 4717700

[51] Int. Cl.⁶ .......................... C12P 21/00; C12N 9/00; C12Q 1/68
[52] U.S. Cl. ........................... 435/68.1; 435/69.1; 435/6
[58] Field of Search ....................... 435/69.1, 69.4, 435/175, 182, 68.1; 935/17

[56] References Cited

U.S. PATENT DOCUMENTS 4,225,671 9/1980 Puchinger et al. ................... 435/71
4,668,624 5/1987 Roberts ................................ 435/68

OTHER PUBLICATIONS

Jagus, R.; Methods Enzymol 152:267–276 (1987).
Baranov, V. I. et al.; Gene 84:463–466 (1989).
Spirin, A. S.; Science 244:1162–1164 (1988).
Gisby, P. E. et al.; Methods Enzymol. 135:440–454 (1987).
Kigawa, T. et al.; J. Biochem. 110:166–168 (1991).
Ryabova, L. A. et al.; Nucleic Acids Res. 17:4412 (1989).
Lim et al., J. Pharm. Sci.. 70:351–354.
Bucke, Meth. Enzymol. 135:175–188.

*Primary Examiner*—Robert A. Wax
*Assistant Examiner*—Eric Grimes
*Attorney, Agent, or Firm*—Peter J. Dehlinger

[57] ABSTRACT

Cell-free production of protein is provided by employing a barrier which defines a reaction region for maintaining the high molecular weight components of the cell-free system while providing means for replenishing loss of low molecular weight components and removing low molecular weight products. Various configurations may be employed for continuous removal and addition of material during the polypeptide synthesis. Conveniently, porous membranes, hollow fibers, or other barriers may be employed. High ratios of peptide to RNA template result.

6 Claims, 4 Drawing Sheets

METHOD OF PREPARING POLYPEPTIDES IN CELL-FREE TRANSLATION SYSTEM

This application is a continuation of application Ser. No. 07/899,826 filed Jun. 16, 1992 now abandoned, which is a continuation of application Ser. No. 07/441,071 filed Nov. 22, 1989 now abandoned, which is a continuation-in-part of U.S. application 07/294,551 filed Dec. 21, 1988, now abandoned, and has a priority based on Russian application No. 4717700 filed Jul. 31, 1989, Russian application No. 4618624, filed Dec. 22, 1988, and Russian application No. 4239148, filed Apr. 29, 1987.

TECHNICAL FIELD

The field of this invention relates to synthesis of polypeptides.

BACKGROUND

The biological revolution has led to the ability to determine natural proteins, to modify such natural proteins to change their properties, and to synthesize new proteins to obtain unique properties. The size of the proteins of interest may vary from small oligopeptides of about 14 amino acids or more, such as somatotropin, angiotensin, bradykinin, etc. to proteins of 300 kD (kiloDaltons) or greater. Chemical synthesis has been developed to the point of automation, where small oligopeptides can be efficiently synthesised. However, as the polypeptide chain is extended, the yield of the end product decreases exponentially with increasing length of the polypeptide chain. This is due to racemization of the amino acid α-carbon, incomplete elongation of individual polypeptide chains, inaccurate bonding and removal of protective groups, and the like. These factors impose serious difficulties on the purification of the end product and drastically increase the cost of the polypeptide product. Impurities having a different amino acid sequence from the desired sequence can have detrimental effects in the case of therapeutic polypeptides.

Expression of polypeptides or proteins in microorganisms by means of genetic engineering also has numerous limitations. These are associated with difficult isolation of the expression product from the transformed cells, lethality of the DNA sequence or product on the host cell, proteolytic degradation of the expression product, and difficulties in isolation and purification of the product from the host proteins. Small polypeptides are readily degraded by the intra- and intercellular proteases due to the absence of a compact spatial structure of the polypeptides.

There is, therefore, substantial interest in finding alternative techniques which allow for the efficient production of polypeptides while lacking one or more of the difficulties associated with present day techniques.

Relevant Literature

A cell-free translation system from wheat germ has been used for the production of rabbit globin polypeptide (Roberts and Paterson, *Proc. Natl. Acad. Sci USA* (1973) 70:2330–2334). Cell-free systems for the expression of polypeptides from messenger RNA have been described by Clemens, *Transcription and Translation: A Practical Approach*, eds. B. D. Hames and S. J. Higgens, IRL Press, Oxford, Chapter 9, pages 231–270. See also, Spirin et al., *Science* (1988) 242:1162–1164; Findeis and Whitesides, *Applied Biochemisty and Biotechnology* (1987) 15:169–189; Riordan, *Biotechnology* (1987) 5:442–448; U.S. Pat. No. 4,668,624; Gavrilova and Smolyaninov, *Molek. Biol.* (1971) 5:883–890; and Fiera et al., *Nature* (1976) 260:500–507.

SUMMARY OF THE INVENTION

Polypeptides are efficiently synthesized from messenger RNA in a cell-free expression system by maintaining during the period of expression the necessary components of the expression system at an efficient level, while removing at least a portion of the lower molecular weight inhibitory products which are produced. Particularly, ribosomes, mRNA, tRNAs and other higher molecular weight products are maintained in a reactor region, while lower molecular weight products such as amino acids and nucleotide triphosphates are replenished and small molecular weight products are withdrawn from the region.

DESCRIPTION OF SPECIFIC EMBODIMENTS

A reactor system is provided comprising the necessary components for expression of a polypeptide from an RNA template in a reactor region over the period of expression, while removing lower molecular weight products of the expression reaction from the reactor region. The reactor region contains those components of the expression system found normally in cells, either prokaryotic or eukaryotic, frequently referred to as cell-free lysates or cell-free expression systems. The concentration of the various components necessary for expression are maintained at at least an efficient level during the course of the expression, while low molecular weight products which tend to inhibit or reduce the efficiency of the reaction are continuously removed from the reactor region. Various methods are employed to segregate the reactor region and maintain the necessary components for the desired or optimal level of expression in the reactor region or provide for such components during the course of the reaction.

The cell-free translation system which can be obtained from procaryotes or eucaryotes include bacteria, such as *E. coli*. Eukaryotic systems include fungi, mammalian cells, e.g., reticulocytes, endothelial cells, and lymphocytes; immortalized cell lines, e.g., cancer cell lines, etc.; plant cells, such as wheat germ or embryo cells, etc. The source of the components may be the cells, may be obtained as a result of recombinant technology, may be synthesized, or combinations thereof, depending upon the particular system employed. Where the cell-free expression system is obtained as a lysate from a cell, the cell may be degraded by any convenient means, such as mechanical disruption, osmolysis, removal of cell walls by appropriate saccharidases, e.g., lysozyme, zymogen, etc., followed by osmolysis, extraction from mechanically-degraded cells, etc. The particular manner in which the cell wall and membrane is broken is not critical to this invention, so long as the components necessary for expression are maintained in an active form and the method of destroying the integrity of the cell does not result in the formation of significant amounts of inhibitors. In addition, it will frequently be desirable to remove endogenous mRNA by means of nucleases, oligo-dT binding and separation, or the like.

Based on the source of the cell-free extract, the proportion of the reaction medium employed will vary. Generally, a cell-free extract will provide at least about 20% of the volume of the reaction mixture and not more than about 70%, generally from about 40 to 60%. In some systems, this may translate from about 0.25 to 0.75 nanomoles/ml of ribosomes. The tRNAs which are present representing all of the codons necessary for expression of the desired peptide will generally be present in total amount in from about 0.1 to 1 mg/ml. The message RNA, may be endogenous or exogenous, and when added will be present in from about 0.01 to 0.5 nmole/ml, preferably from about 0.05 to 0.2 nmole/ml. In some instances, the system will provide for both transcription and translation, where the DNA comprising the gene(s) which is added will generally be present in from about 0.1 to 0.5 mg/ml. The various triphosphates, particularly ATP and GTP, but also UTP and CTP will be present for transcription, with ATP in an amount of from about 0.5 to 5, more usually about 1 to 2 mM while the other triphosphates will generally be present, when present, in amounts from about 0.05 to 1 mmole/ml.

Normally a source of a high energy phosphate bond will be provided, such as creatine phosphate or phosphoenol pyruvate or the like, along with enzymes which provide for the formation of such high energy phosphate bonds, such as creatine phosphokinase and pyruvate kinase, respectively.

The individual amino acids, which may be natural or unnatural (where a tRNA can be produced), will be present at a concentration in the range of about 0.10 to 25, preferably about 0.20 to 10 μm. The solution will be buffered, generally having from about 10 to 100 mmole of a buffer, particularly a nitrogen amino buffer such as Tris or HEPES. The pH will generally be in the range of about 7 to 9, preferably about 7.25 to 8.5. Magnesium will generally be present in at least about 1 mmole and not more than about 20 mmole. Other salts will also be present, such as potassium acetate, ammonium chloride, calcium chloride, or the like, where the total amount will generally range from about 50 mM to 200 mM.

Normally added to the mixture will be various inhibitors, to prevent degradation of the various components in the reaction region. Thus, sufficient amounts of protease and RNase inhibitors will be provided in the reaction mixture. The RNase inhibitors will generally range from about 1 to 20 μg/ml, while the protease inhibitors will generally range from about 0.05 to 0.5 μg/ml.

For procaryotic cell-free systems, fraction S100 will normally be present in amount of at least about 0.2 mg/ml, and not more than about 2 mg/ml, preferably about 0.5–1.5 mg/ml.

In addition, various additives may be added to the cell-free system for a variety of reasons. Polyols, such as glycerol, polyethylene oxides, or the like, may be included in from about 0.5 to 2.5 vol %, preferably not more than about 2 vol%. Small amounts of a reductant, particularly a mercaptide may be employed, such as dithiothreitol, generally in an amount of from about 1 to 10 mmoles/liter. Also, spermidine or other polyalkylenepolyamine may be employed, generally in amounts of from about 0.1 to 0.5 mmole/ml. Other components include synthetases which join the appropriate amino acid to the tRNA.

For the most part, the various components have been described in the literature and have been previously employed in other cell-free systems.

Where both transcription and translation are involved, the system will include all the necessary ribonucleotide triphosphates at the concentrations indicated above. The cell-free lysate will not only include the translation system based on the ribosome, but also the transcription system employing an RNA polymerase. The DNA employed will include transcriptional and translational regulatory regions recognized by the RNA polymerase, e.g., promoter, terminator, start site, Shine-Dalgarno sequence, etc., as well as a structural gene or open reading frame with initiation and stop codons, under the regulatory control of the regulatory regions.

The concentrations of the reactants and the products in the reaction region will be controlled by transport of compounds across a porous barrier. By providing for a porous barrier which has a molecular weight cutoff of less than about 100 kD, preferably less than about 50 kD, but greater than about 1–5 kD, one can provide for the replenishment of the small molecular weight reactants, while removing the small molecular weight products, which result in the inhibition of expression of the desired product. By small molecular weight is intended less than about 10 kD, usually less than about 5 kD, usually about 0.1 to 3 kD. The barrier may provide a cutoff for ribosomes, or mRNA or tRNA or enzymes, where the lowest molecular weight species cutoff will provide a barrier for all of the higher molecular weight species.

Barriers may be provided in a variety of ways, such as porous membranes, porous particles, hollow fibers, fritted discs, or the like. The porous barrier may be a single or multiple layer, may be in the form of sheets, particles, hollow fibers, tubes, or the like. Numerous configurations may be designed which allow for maintenance of the desired components in the reaction region with the removal of the undesired components from the reaction region. By providing for a source of the low molecular weight reactants to the reaction region, so as to replenish or augment the depletion of such components during the course of the reaction, while at the same time removing the low molecular weight products of the reaction, one can greatly extend the course of the period of expression and provide for high molar ratios of protein product to template present in the reaction medium.

Membranes which may be used include Amicon XM-100, ultrafiltration membranes, and hollow fibers such as Amicon H-1, P-100 and MP-01.

The simplest configuration is a membrane bag containing the reaction region, while retaining a solution outside the membrane which provides for the desired level of the lower molecular weight reaction components in the reaction region. Thus, by exchange across the membrane, the lower molecular weight products produced by the reaction will be continuously dialyzed into the external solution, while the reaction components will be continuously replenished in the reaction region. The lower molecular weight components to be removed will for the most part be mono- and diphosphates, such as adenosine monophospate and diphosphate, guanosine diphosphate, inorganic phosphate, pyrophosphate, and the like. By having a continuously flowing external solution, where the flow rate can be maintained at a controlled flow rate, the exchange may be monitored and equilibrium maintained between the reaction region and the external solution. For a 1 vol reaction region, flow rates of 0.1 to 50 or more vol/h of an external solution, having the buffer and other lower molecular weight reactants or components necessary for expression, may be employed.

Another configuration would employ a reaction solution containing the lower molecular weight reaction components continuously introduced into the reaction region, while the same volume of liquid containing the lower molecular weight products is continuously withdrawn from the reaction region. Thus, by having rates of about 0.1 to 50 or more vol/h per volume of reaction medium, one can maintain the desired concentrations in the reaction.

Hollow fibers may be employed, where the reaction region may be the lumen of the hollow fiber or outside the lumen, while the solution containing the lower molecular weight reactants will be outside the lumen or inside the lumen, respectively. Alternatively, one may use membrane sheets where the sheets may alternately define the reaction region or the lower molecular weight reactant component solution.

If desired, the ribosome may be restrained by covalent or non-covalent binding to a solid surface. The solid surface may take the form of hollow fibers, membranes, porous ceramics and the like. Restraint may be achieved by employing antibodies to the ribosome which do not interfere with ribosomal activity. Covalent binding may be achieved by employing activated surfaces to which the ribosome may be bound. Particles may be prepared which will encapsulate the ribosome, while allowing for free access of the other higher or lower molecular weight reaction components, such as tRNA, mRNA, amino acids, nucleotide triphosphates, and the like. Alternatively, the message RNAs, tRNAs, the synthases for bonding the amino acids to the appropriate tRNA, etc., may also be immobilized within the particles, which may be referred to as microgranules or microcapsules. The microgranules or microcapsules will generally be of a size and the range of about 0.1 μm to 10 μm or more.

Various materials may be employed for preparation of the particles. The particles may be formed by polysaccharides, and/or polymers or polymer complexes, particularly where the particle forming material is charged. Materials which may find use include combinations of alginate and poly-L-lysine. By combining the components of the reaction medium with the particle forming mixture, for example, the cell-free reaction mixture may be combined with an equivolume 1 to 5 percent solution of sodium alginate. After adding a cross-linking amount of calcium salt, generally a solution of about 0.5 to 2.5% calcium salt, the resulting particles are washed, followed by the addition of a dilute solution of poly-L-lysine, generally being from about 0.01 to 0.1%. The polylysine will usually be at least about 10 kD and not more than about 100 kD. The particles may then be washed with an appropriate buffer, followed the addition of about 0.2 to 1% polyimine P solution. The particles may then be washed and are ready for use for production of protein. Conveniently, the particles may be introduced into a column and the necessary lower molecular weight reaction components passed through the column for synthesis of the desired protein.

Another configuration could provide for a sheet where ribosomes are bound by antibodies or other convenient means, either directly or through membranous material, such as endoplasmic reticulum, where spaced apart from the ribosome support sheet are two porous sheets having molecular weight cutoffs of at least about 5 kD, preferably at least about 7.5 kD, but which will retain molecules such as mRNA, tRNA, enzymes, such as aminoacylsynthethases, and the like. External to the porous membranes would be an enclosure for the passage of the lower molecular weight species, so as to maintain an equilibrium concentration within a predetermined range of the various lower molecular weight reactants with removal of the lower molecular weight products. In this manner, one could have two flow streams, a relatively slow stream which is in contact with the ribosomes and continuously but slowly exchanges various of the higher molecular weight components of the reaction system, while also removing product from the reaction region, and a somewhat faster stream which provides for the exchange of the lower molecular weight materials.

The system described above could be readily modified using hollow fibers, where one fiber could be in contact with the free space of the container or enclosed within a second fiber which may or may not be porous, where the ribosome would be retained in the lumen. The lumen would provide for flow of the higher molecular weight components within the lumen, where a slow stream would be permitted for removal of product from the lumen and recirculation of the other components of the reaction. The second stream would be external to the hollow fiber and would provide the necessary lower molecular weight reactants with removal of the lower molecular weight products.

Other configurations may also be devised, where one can provide for replenishment of lower molecular weight reactants, and removal of lower molecular weight products, while retaining the higher molecular weight components within an enclosure. In addition, one can provide for two stages, where one can provide for a slow circulation of one or more of the higher molecular weight components within an enclosure, while at the same time providing in a separate system for addition of lower molecular weight reactants and removal of lower molecular weight products.

The temperature for the reaction will generally be in the range of about 20° to 40° C., more usually in the range of about 25° to 37° C. Ambient pressures may be employed, although in some instances, higher or lower pressures may be desirable. The time of the reaction will usually be at least 10 hours, more usually at least 20 hours, preferably at least 40 hours, and may be 50 hours or more. The yield will be at least 100 polypeptide molecules per mRNA usually at least 200 molecules per mRNA, and may be 300 molecules or more for mRNA.

The subject methodology may be used to prepare any protein of interest, where processing of the protein is not required or may be carried out during the formation of the protein in the subject reaction mixture or in a subsequent reaction step. By processing is intended glycosylation, peptide cleavage, methylation, acetylation, or the like. Proteins of interest include various mammalian proteins, such as interferons, colony stimulating factors, interleukins, hormones, e.g., growth hormone, growth factors, e.g., EGF, TGF, etc., enzymes, e.g., chymosin, super oxide dismutase, lipases, proteases, etc., surface membrane proteins, e.g., CD4, CD8, sIg, receptors, e.g., growth factor receptors, G proteins, addressins, adhesion molecules, plasminogen activators, blood factors or the like.

The cell-free system may be readily prepared in accordance with conventional methods. See particularly, Clemens, Translation of Eukaroytic Messenger RNA in Cell-Free Extracts, in *Transcription and Translation: A Practical Approach*, eds. B. D. Hames and S. J. Higgins, Chapter 9, 231–270, IRL Press, Oxford. The reticulocyte and the wheat germ cell-free systems, and the nuclease treated systems are commercially available from a wide variety of sources. The conditions for preparing these compositions are also defined in the article. Further purification of the cell-free systems may be desirable, for example, by removing low molecular weight RNA fragments from nuclease treatment using for example, gel separation, oligo-dT separation, etc.

Other cell-free systems may be employed, such as Ehrlich ascites, tumor cell extracts (Clemens, pp 246), stripped microsomal membranes from dog pancreas (Clemens, pp 258) or any other cell-free system which may be developed.

The following examples are offered by way of illustration and by limitation.

EXAMPLES

Example 1

1 ml of a cell-free translation system contains 0.6 nmole of 70S ribosome of *E. coli*, 1 mg of fraction S 100, 0.6 mg of tRNA, 0.06 nmole of mRNA phage MS2 cell protein, 5 µg of pyruvate kinase, 2–10 µg of ribonuclease inhibitor from the human placenta, and 0.1 µg of protease inhibitor (aprotinin, leupeptin, chymostatin) in the following buffer solution: 20 mM of Tris-HCl, pH 7.4, 100 mM of $NH_4Cl$, 10 mM of $MgCl_2$, 2 mM of ATP, 0.2 mM of GTP, 5 mM of phosphoenolpyruvate, 25 µM of [$^3$H]-leucine (the specific activity equals 52 Ci/nmole) and 25 µM of each of the remaining 19 amino acids.

The cell-free translation system is placed in a cell for ultrafiltration and polypeptide is synthesized at a temperature of 37° C. The translation products, including the end product and the products of decomposition are withdrawn from the system through a semipermeable membrane with simultaneous delivery of a mixture of substrates in the form of ATP, GTP and amino acids into the reaction system during 20 hours. As a result, phage MS2 cell protein is obtained.

During the entire duration of the synthesis, the end product is synthesized at a constant rate. The quantity of the obtained protein per mRNA unit depends on the time for the synthesis.

As a result, 6000 picomoles of cell protein was obtained during the time of work of the cell-free translation system from *E. coli*, 100 picomoles of the end product per picomole of mRNA of phage MS2 cell.

Example 2

Calcitonin is prepared by the method described in Example 1, except that 0.06 nmole of calcitonin mRNA is used instead of mRNA of phage MS2 cell protein. The peptide calcitonin is obtained by the synthesis. During the entire duration of the synthesis, forty hours, the rate of production remains constant. 18000 picomoles of calcitonin are prepared during the operation of the cell-free translation system from *E. coli*. This is 300 picomoles of the end product per picomole of calcitonin mRNA.

Example 3

1 ml of a cell-free translation system contains 0.5 ml of wheat germ extract, 0.1 nmole of viral mRNA, 64 µg of creatine phosphokinase, 2–10 µg of ribonuclease inhibitor from the human placenta, and 0.1 µg of each of the protease inhibitors (aprotinin, pepstatin, leupeptin) in a buffer solution of the following composition: 40 mM HEPES, pH 7.6, 112 mM KOAc, 1.9 mM MgOAc, 0.25 mM spermidine, 6 mM of dithiotreitol, 1.5% of glycerol, 2 mMATP, 50 µM GTP, 8 mM creatine phosphate, 25 µM [$^3$H]-leucine (the specific activity, 50 Ci/nmole) and 25 µM of each of the remaining 19 amino acids.

The cell-free translation system is placed in a cell for ultrafiltration and polypeptides are synthesized at a temperature of 25° C. The translation products, including the end product and the degradation products are withdrawn through a semipermeable membrane with simultaneous delivery of the substrates in the form of ATP, GTP and amino acids into the system for 20 hours. The resulting product is protein of the BMV virus. During the entire time of work of the system the synthesis rate remains the same. 10000 picomoles of protein of BMV virus is prepared during the operation of the cell-free translation system, which is 100 picomoles of the end product per picomole of viral mRNA.

Example 4

Calcitonin is prepared by the method described in Example 3 except that 0.1 nmole of calcitonin mRNA is used instead of viral mRNA. During the entire time of the work of the translation system, forty hours, the end product is synthesized at a constant rate. 15000 picomoles of calcitonin were synthesized in the wheat germ cell-free translation system which is 150 picomoles of the end product per picomole of mRNA of calcitonin.

Electrophoretic analysis was performed of the synthesized polypeptides.

The analysis shows that the synthesized polypeptides have the molecular weight corresponding to their natural analogues.

Example 5

Calcitonin synthesis in the cell-free eukaryotic translation system from wheat embryos immobilized in microcapsules from Na-alginate and polylysine.

Wheat embryo lysate is prepared as described in Roberts and Paterson, (1973) *Proc. Natl. Acad. Sci. USA*, 70:2330–2334. Calcitonin mRNAs are obtained according to Melton et al., (1984) *Nucl. Acids. Res.*, 12:7057–7070. Solution A contains 35 mM HEPES, pH 7.7, 2.1 mM $Mg(OAc)_2$, 70 mM KOAc, 1 mM ATP, 25 µM GTP, 250 µM spermidine, 25 µM [$^3$H]-leucine (specific radioactivity 24 Ci/nmol), 25 µM each of the remaining 19 amino acids, 8 mM creatine phosphate. 25 ml of the incubation mixture prepared from solution A contains 80 optical units of $A_{260}$ wheat embryo lysate (S-30), 80 pmol of calcitonin mRNA, and 150 units of activity of ribonuclease inhibitor from human placenta. The obtained incubation mixture is immobilized in alginate-poly-L-lysine capsules according to Gilligan et al., (1988) *In Vitro Cellular and Developmental Biology*, 24:35–46. 2.5 ml of the incubation mixture are mixed with 2.5 ml of 2% Na-alginate. The obtained mixture is introduced into a 1.2% calcium chloride solution through a dropping funnel. The obtained microgranules are washed thrice with a solution containing 120 mM KOAc and 2 mM $Mg(OAc)_2$. The wash solution is removed and 0.025% poly-L-lysine (molecular weight-50000) is poured onto the granules, which are then incubated for 6 minutes. After removal of poly-L-lysine solution, the granules are washed twice with buffer, placed in 0.6% polyimine P solution in 120 mM KOAc and incubated for 4 minutes. Polyimine is removed, the mixture is washed once with buffer and thrice with 50 mM potassium citrate, pH 7.5. The resulting microcapsules are placed in a chromatography column and washed twice with buffer A. Then buffer A is passed through the column at 3 ml/h. The yield from the column is stored and analyzed for the presence of the synthesized product. The reaction is carried out at 25° C. for 100 hours with a substantially linear increase in mols of peptide per mol mRNA. As a result, 32000 pmol were synthesized for 100 hours.

Example 6

Cell-free prokaryotic system of translation of the MS2 phage coat protein on the mRNA template of MS2 phage in a continuous-action device with an incubation mixture encapsulated in alginate gel.

The standard cell-free system of translation was prepared as described (Gavailova and Smolyaninov, (1971) *Molek. Biol.* 5:883–890). MS2 RNA was obtained according to Fiera et al., *Nature* (1976) 260:500–507.

1 ml incubation mixture containing 0.6 nmol 70S ribosomes, 1 mg S100 fraction, 0.6 mg tRNA, 0.06 nmol mRNA of MS2 phage coat protein, 5 µg pyruvate kinase, 2 to 10 µg ribonuclease inhibitor from human placenta, 0.1 µg each of the protease inhibitors (aprotinin, leupeptin, chymostatin) in buffer A: 20 mM Tris-HCl, pH 7.5, 10 mM $MgCl_2$, 100 mM $NH_4Cl$, 1 mM ATP, 0.2 mM GTP, 5 mM phosphoenolpyruvate, 25 µM [$^3$H]-leucine (specific radioactivity 52 Ci/mmol) and 25 µM each of the remaining 19 amino acids.

The incubation mixture was polymerized in a 15 ml column in several stages, after each step the column was washed with 10 ml buffer A, all the procedures were performed at 4° C. At the first stage 1 ml of 2% Na-alginate solution in buffer A was added to the mixture, then the mixture was layered on a column filled with 10 ml of 50 mM $CaC_{12}$ solution in buffer A. The solution was introduced to the column slowly, in portions so that polymer balls of small dimensions could be formed. At the second stage 10 ml of 0.02% polylysine solution in buffer A were introduced in the column and the mixture was incubated for 5 minutes. At the third stage 10 ml of 0.2% polyimine solution in buffer A were introduced in the column and the mixture was incubated for 3 minutes. At the fourth stage 50 mM of sodium citrate, pH 7.5, were introduced in the column and the mixture was incubated for 2 minutes. Finally, the column was washed with 20 ml of buffer A.

The synthesis in the column was carried out at 37° C. The separation of the final product as well as the decomposition products was performed by passing though the column at 4 ml/h a supply of buffer A.

The product synthesis proceeded at a constant rate. As a result, for 100 hours about 30000 pmol coat protein was synthesized in the column.

Example 7

Expression of genes of the plasmid pUD 18 in a cell-free system.

A standard cell-free system was prepared for combined transcription/translation. The plasmid pUD 18 contains genes of β-lactamase and dihydrofolate reductase.

The solution (A) contains 55 mM of Tris-acetate, pH 8.2, 11 mM of MgOAc, 9.5 mM of $CaCl_2$, 76 mM of KOAc, 1.5 mM of DDT (dithrothreitol), 1.6% of polyethylene glycol 6000, 5 mM of phosphoenolpyruvate, 1.2 mM of ATP, 0.8 mM of each of GTP, CTP and UTP, 5 µg/l of folic acid, 100 µM of [$^3$H]-leucine (specific radioactivity of 230 mCi/mmol) and 100 µM of each of the remaining aminoacids. 1 ml of the reaction mixture prepared using the buffer (A) contains 430 µl of the extract S30, 150 µg of the plasmid pUD 18, and 200 µg of total tRNA.

The standard system of combined transcription/translation synthesized 6 picomoles of each of β-lactamase and dihydrofolate reductase per ml of the incubation mixture over 40 minutes of incubation at a temperature of 37° C.

Figure 1:
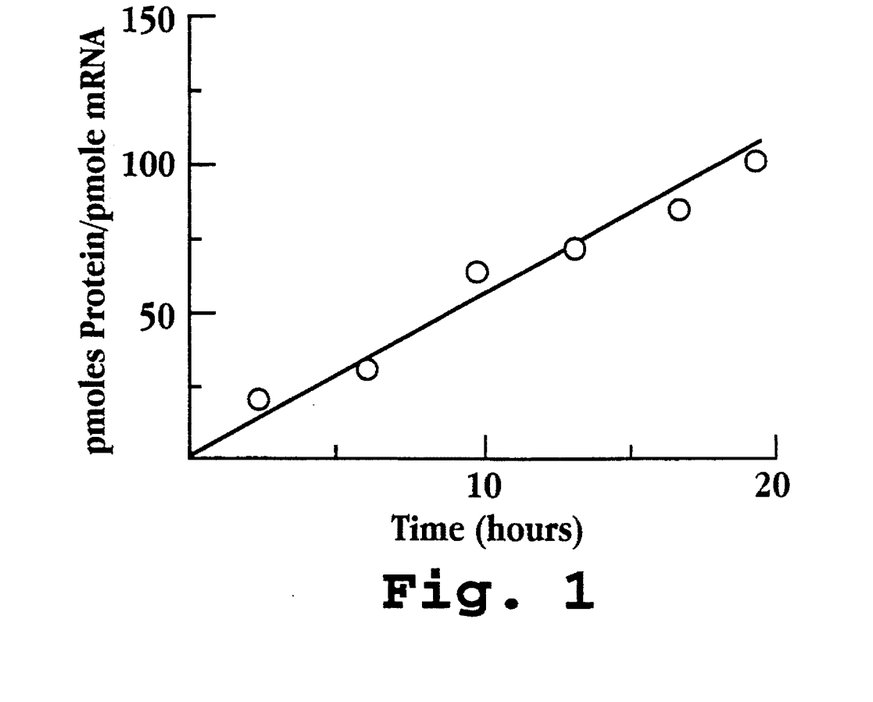
FIG. 1 shows a plot of protein per mRNA (pmoles protein/pmole mRNA) on the ordinate vs. time in hours (abscissa) as described in Example 1.
Figure 2:
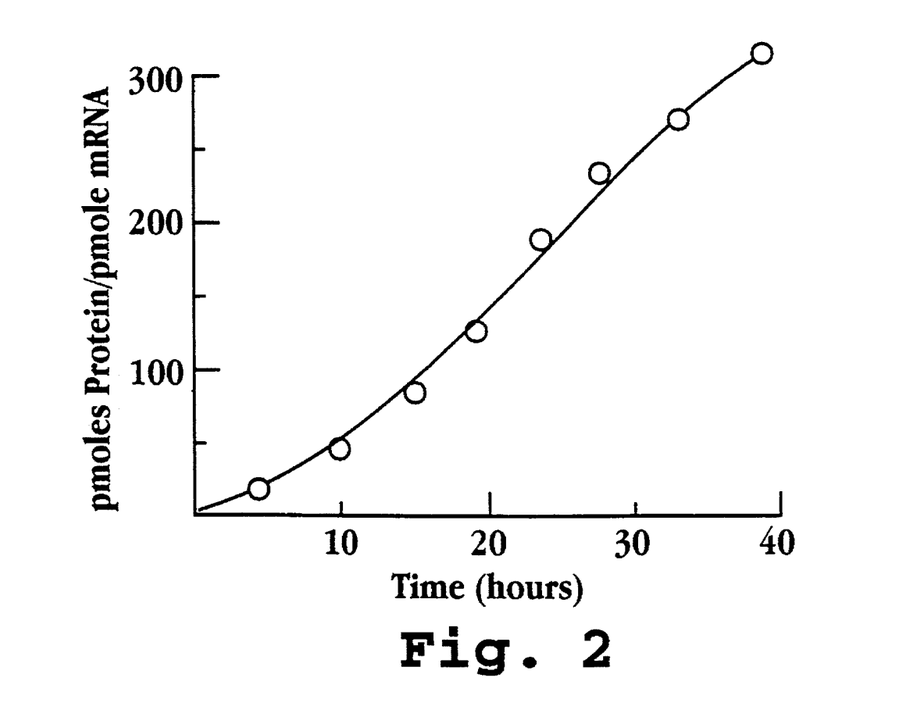
FIG. 2 shows a plot of calcitonin produced in an E. coli translation system (pmoles protein/pmole mRNA) versus time in hours, in accordance with the description in Example 2.
Figure 3:
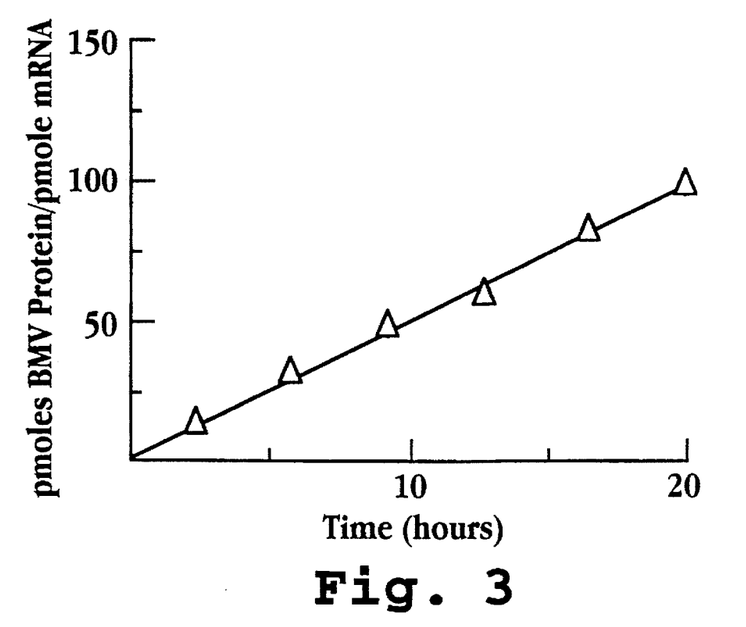
FIG. 3 shows a plot of BMV protein produced in a wheat germ extract system (pmoles BMV protein/pmole mRNA) on the ordinate versus time in hours (abscissa), in accordance with the description in Example 3.
Figure 4:
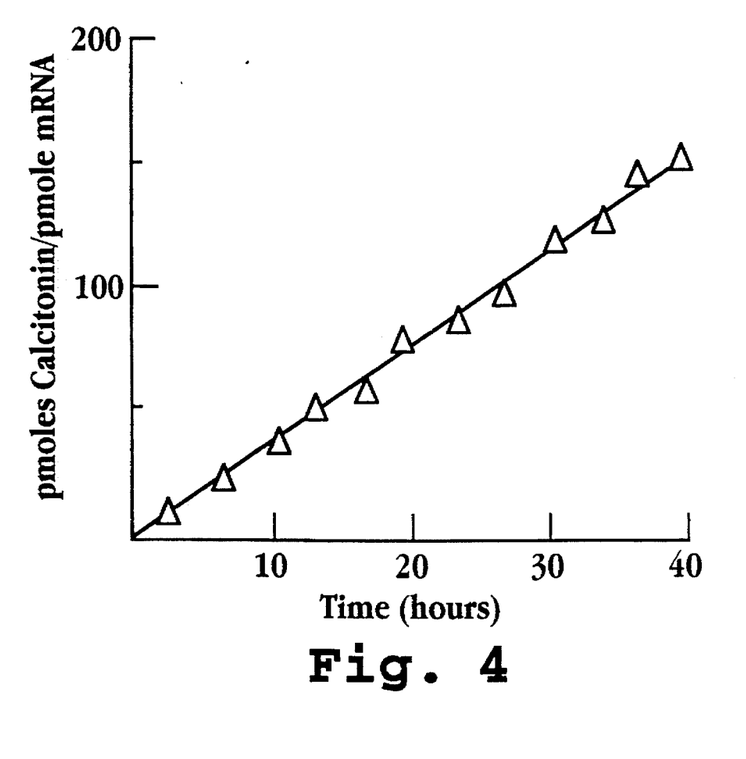
FIG. 4 shows a plot of calcitonin produced in a wheat germ extract translation system (pmoles calcitonin/pmole mRNA) on the ordinate versus time in hours (abscissa), in accordance with the description in Example 4.
Figure 5:
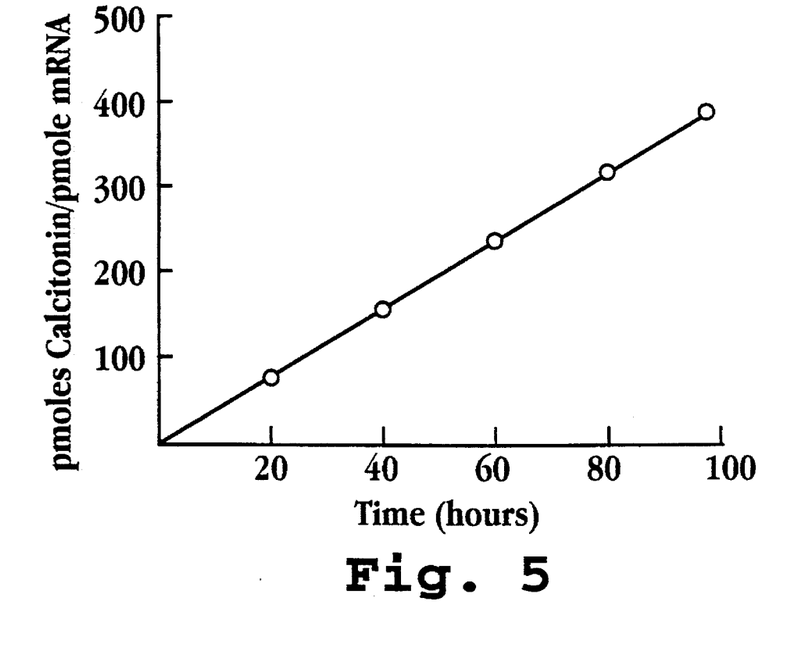
FIG. 5 shows a plot of calcitonin synthesis in a wheat germ extract translation system immobilized in microcapsules of alginate and polylysine, where the ordinate values are pmoles calcitonin/pmole mRNA and the abscissa represents time in hours, in accordance with the description in Example 5.
Figure 6:
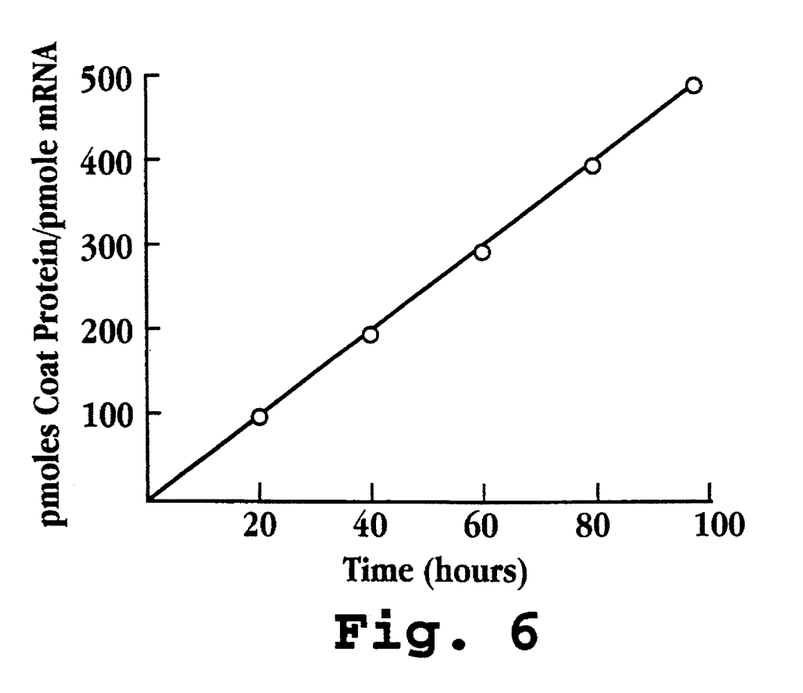
FIG. 6 shows a plot of production of MS2 coat protein in a cell-free translation system immobilized in a column, as described in Example 6, where the abscissa represents pmoles of coat protein per pmole mRNA and the ordinate represents time in hours.
Figure 7:
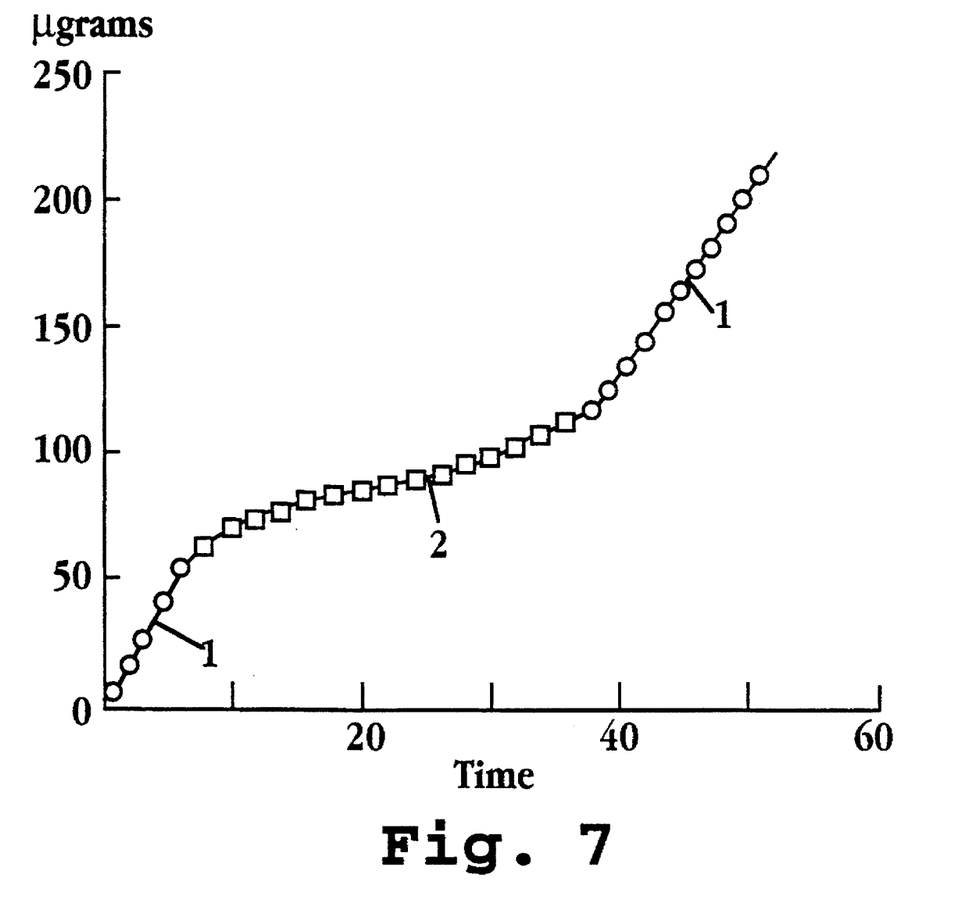
FIG. 7 shows a plot of protein produced (micrograms) as a function of time in hours in the combined transcription/translation system described in Example 9, where region 1 of the curve shows production when reactants were added at a rate of 3 ml/hour and region 2 shows production when reactants were added at a rate of 2 ml/hour.

In a parallel experiment in a continuous action unit, the solution (A) was continuously added to 1.0 ml of the reaction mixture at the rate of either 3 ml/h or 2 ml/h and the reaction products were withdrawn at the same rate through an ultrafiltration membrane XM-100 (Amicon). The kinetics of expression of genes of β-lactamase and dihydrofolate reductase in such system is graphed, wherein the synthesis time t is plotted along the abscissae, while the amount of the formed products in micrograms is plotted along the ordinate (FIG. 7). In the initial phase (0–8 h) the solution (A) is supplied at the rate of 3 ml/h, in the next phase (8–35h) the solution (A) is delivered at the rate of 2 ml/h. The rate of synthesis of polypeptides is shown to depend on the rate of supply of the solution (A), but does not depend on the time of functioning of the system.

In over 50 hours of functioning of such system in a 1 ml reaction mixture, there is synthesized 4.1 nanomoles of each of β-lactamase and dihydrofolate reductase, which corresponds to 212 µg of the proteins β-lactamase and dihydrofolate reductase.

Therefore, the method according to the present invention provides expression of genes in a cell-free system with synthesis of the product in an amount more than 500 times greater than the standard cell-free system of conjugated transcription/translation.

It is evident from the above results, that substantially improved expression of protein products can be achieved in the absence of cells. Thus, one can avoid the contamination resulting from cell debris and cell proteins when purifying the product, can provide for high yields of product in relation to the amount of message introduced into the cell-free system, and for smaller products, avoid degradation and provide for continuous removal of the product from the reaction system. In addition, one avoids the waste of nutrients required for the growth of organisms and the uncertainties involved with synthetic procedures. By employing the subject invention, substantial efficiencies are achieved for the production of proteins, from both natural and synthetic genes.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. In a method for producing a polypeptide by preparing a reaction mixture containing a source of mRNA which encodes the polypeptide in a cell-free peptide synthesis system which includes ribosomes, tRNA, amino acids, ATP, and GTP in an aqueous buffer, where the mRNA is one capable of being translated to form the polypeptide in such as system, and incubating said reaction mixture under conditions in which polypeptides and lower molecular weight products are produced, the improvement comprising during said incubating, removing components which are able to pass through a semi-permeable barrier permeable to components having molecular weights up to 100,000 daltons, and adding ATP, GTP, and amino acids to the ribosomes in the reaction mixture to replenish such removed components in the reaction mixture, and by said removing and adding, achieving continuous production of the polypeptide for at least several hours.

2. The method of claim 1, wherein the peptide synthesis system includes a bacterial cell extract, ribosomes, mRNA and tRNA.

3. The method of claim 1, wherein the peptide synthesis system includes a wheat germ extract, ribosomes, mRNA and tRNA.

4. The method of claim 1, wherein said semi-permeable barrier is an ultrafiltration membrane.

5. The method of claim 1, wherein production of the polypeptide is carried out continuously for at least 40 hours.

6. The method of claim 1, wherein the cell-free peptide expression system comprises a transcription/translation system, and said source of mRNA includes a DNA which encodes said polypeptide, an RNA polymerase enzyme, and ribonucleotides.

* * * * *